United States Patent
Janson et al.

[11] Patent Number: 5,961,554
[45] Date of Patent: Oct. 5, 1999

[54] INTERVERTEBRAL SPACER

[76] Inventors: Frank S Janson, 1519 Prospect Ave., Rocky River, Ohio 44116; Albert N. Santilli, 28326 Gates Mills Blvd., Pepper Pike, Ohio 44124

[21] Appl. No.: 08/778,023

[22] Filed: Dec. 31, 1996

[51] Int. Cl.$^6$ ................................................ A61F 2/44
[52] U.S. Cl. ........................... 623/17; 623/16; 606/61
[58] Field of Search ......................... 623/17, 16, 11, 623/18; 606/60, 61, 76

[56] References Cited

U.S. PATENT DOCUMENTS

| | | | |
|---|---|---|---|
| 3,855,638 | 12/1974 | Pilliar | 623/16 |
| 3,906,550 | 9/1975 | Rostoker et al. | 623/16 |
| 4,429,691 | 2/1984 | Niwa et al. | 128/92 C |
| 4,542,539 | 9/1985 | Rowe, Jr. et al. | 623/16 |
| 4,693,721 | 9/1987 | Ducheyne | 623/16 |
| 4,714,469 | 12/1987 | Kenna | 623/17 |
| 4,743,256 | 5/1988 | Brantigan | 623/17 |
| 4,878,915 | 11/1989 | Brantigan | 623/17 |
| 5,071,437 | 12/1991 | Steffee | 623/17 |
| 5,171,281 | 12/1992 | Parsons et al. | 623/17 |
| 5,192,326 | 3/1993 | Bao et al. | 623/17 |
| 5,201,766 | 4/1993 | Georgette | 623/16 |
| 5,222,983 | 6/1993 | Schmitz et al. | 623/16 |
| 5,306,309 | 4/1994 | Wagner | 623/17 |
| 5,314,478 | 5/1994 | Oka et al. | 623/18 |
| 5,458,638 | 10/1995 | Kuslich et al. | 623/17 |
| 5,458,643 | 10/1995 | Oka et al. | 623/17 |
| 5,514,180 | 5/1996 | Heggeness et al. | 623/17 |
| 5,522,899 | 6/1996 | Michelson | 623/17 |
| 5,534,030 | 7/1996 | Navarro et al. | 623/17 |
| 5,545,229 | 8/1996 | Parsons et al. | 623/17 |
| 5,562,738 | 10/1996 | Boyd et al. | 623/17 |
| 5,571,192 | 11/1996 | Schönhöffer | 623/17 |
| 5,593,409 | 1/1997 | Michelson | 623/17 |
| 5,609,635 | 3/1997 | Michelson | 623/17 |
| 5,665,119 | 9/1997 | Koller | 623/16 |

OTHER PUBLICATIONS

Collis, et al, Anterior Total Disc Replacement: A modified Anterior Lumbar Interbody Fusion, Aspen Public., 1989, pp. 149–152.

Wheeler, et al, Porous Litanium Alloy for Prosthesis attachment, Titanium Alloys in Surgical Implants, 1983, pp. 241–153.

Nakaucki, et al, An experimental study on Titanium Fiber Metal Implant for Spine Fusion in Intersegmental Fusion Model, p. 107 (Publisher & date unknown).

*Primary Examiner*—Michael J. Milano
*Assistant Examiner*—Tram A. Nguyen

[57] ABSTRACT

A porous intervertebral spacer includes a plurality of fused, generally spherical beads of a biologically inert material, preferably titanium or a titanium alloy. The spacer can include elongate, tortuous strands of titanium wire mesh intermixed with the beads. The spacer also can be made entirely of strands of elongate, fused, tortuous titanium wire mesh. A method of fusing adjacent vertebrae of the spine includes the steps of excising a portion of an intervertebral disc separating adjacent vertebrae and portions of the adjacent vertebrae to define a graft bed, and inserting into she graft bed at least one porous intervertebral spacer according to the invention.

34 Claims, 6 Drawing Sheets

INTERVERTEBRAL SPACER

BACKGROUND OF THE INVENTION

1. Field of the Invention

The invention relates generally to an intervertebral spacer and method for spacing and fusing adjacent vertebrae and, more particularly, to a porous, strong, intervertebral spacer formed of a biologically inert material.

2. Description of the Prior Art

Techniques and devices for fusing two or more vertebrae of the spine together are well known. Such techniques are commonly performed to correct problems, such as chronic back pain, which result from degenerated intervertebral discs. One technique for fusing together two or more vertebrae of the lumbar spine includes excising a portion of the disc extending between adjacent vertebrae and grafting one or more portions of bone of a desired shape, known as an intervertebral spacer, between the adjacent vertebrae. The intervertebral spacer may be inserted by either an anterior or posterior approach to the spinal column depending on a number of factors, including the number of vertebrae to be fused and past operative procedures. Upon healing, the vertebrae are desirably fused together through the intervertebral spacer.

Conventionally, intervertebral spacers have been autogenic bone harvested from other areas of the body, such as the pelvis, allogenic bone taken from cadavers or xenogenic bone, such as bovine bone sections. However, the use of bone grafts can add complications to the fusion procedure. For example, when using an autogenic bone graft, a second incision must be made in the patient to harvest the additional bone to be used in the graft, thus increasing the pain and blood loss to the patient. When allogenic or xenogenic bone grafts are used there is a potential for the transmission of disease from the cadaver or other graft source to the patient.

The use of non-biological implants, such as carbon fiber spacers, also has been attempted in the past, but these spacers tend to lack sufficient porosity and tissue ingrowth characteristics to function adequately.

It would be desirable to provide a non-biological spacer which is non-reactive in the body and which has the strength and tissue ingrowth characteristics of a bone graft spacer.

SUMMARY OF THE INVENTION

The present invention provides a porous intervertebral spacer which can be used in the same manner as a bone graft spacer to fuse vertebrae together. The inventive spacer preferably is composed of titanium beads or titanium alloy beads sintered in a mold of a desired shape and size. The spacer is non-biologically reactive and provides for tissue ingrowth to facilitate fusion with adjacent vertebrae.

In accordance with one aspect of the invention, a porous intervertebral spacer is formed in a variety of shapes such as a prism (for example, a rectangular prism), a cylinder, and a plate. In each instance, the spacer is made of a plurality of fused, generally spherical beads of a biologically inert material such as titanium or a titanium alloy.

In accordance with another aspect of the invention a method of fusing adjacent vertebrae of the spine includes the steps of excising a portion of an intervertebral disc separating adjacent vertebra and portions of the adjacent vertebrae to define a graft bed, and inserting into the graft bed at least one porous intervertebral spacer formed from a plurality of fused, generally spherical beads of a biologically inert material such as titanium or a titanium alloy.

In general, the invention comprises the foregoing and other features hereinafter fully described and particularly pointed out in the claims, the following description and the annexed drawings setting forth in detail a certain illustrated embodiment of the invention, this being indicative, however, of but one of the various ways in which the principles of the invention may be employed.

BRIEF DESCRIPTION OF THE DRAWINGS

In the annexed drawings:

FIG. 9M is a view similar to FIG. 9I showing a kidney-shaped spacer;

FIG. 9N is a view similar to FIG. 9M in which ribs have been added to the upper and lower faces of the spacer;

DETAILED DESCRIPTION OF THE INVENTION

Figure 1:
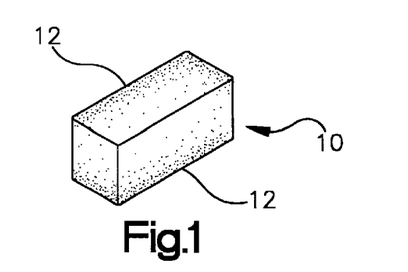
FIG. 1 is a perspective view of an intervertebral spacer in accordance with the invention, the spacer being in the form of a rectangular prism.

With reference to the drawings and initially to FIG. 1, there is shown an intervertebral spacer 10 in accordance with the present invention. The spacer 10 is in the form of a porous biologically inert block in the form of a rectangular prism. The corners of the spacer 10 may be formed with a small radius if desired. One or more such rectangular, block-shaped spacers 10 are sized to fit within an opening or graft bed formed between adjacent vertebrae by the surgical excision of a portion of the intervertebral disc and confronting portions of the adjacent vertebral bodies. The particular size of the spacer 10 will be determined by the particular vertebrae to be fused, and condition of the vertebrae. Advantageously, because the spacers are not made of a biological material, they are easily stored and can be manufactured in a variety of shapes and sizes to accommodate anticipated situations. A typical spacer 10 for fusing vertebrae of the lumbar spine may be from 10 to 13 millimeters in width, 12 to 18 millimeters in height, and 25 to 30 millimeters in length.

It will be appreciated that while the specific example of the intervertebral spacer described herein is with reference to a spacer for fusing vertebrae of the lumbar spine together or to the sacrum, the invention applies also to spacers for fusing vertebrae of the cervical or thoracic spine as well. The particular shape of the spacer is also a function of the application. While a generally rectangular spacer is well suited to fusing lumbar vertebrae, in other instances other shapes for the spacer, such as cylindrical, may be desirable. Moreover, it will be recognized that the spacers of the invention may also be used in other areas of the body to fuse bone together where necessary.

The spacer 10 is preferably composed of biologically inert spheres or beads having a diameter such as to yield, when fused, a spacer with the fused beads occupying a range of generally 45 to 58 percent of the volume of the spacer. This density provides a spacer 10 which is sufficiently porous throughout to allow for the flow of bodily fluids through the spacer and to promote tissue ingrowth and bony fusion with adjacent vertebrae. The beads also result in porcus surfaces 12 over the spacer 10 which when implanted develop a high friction interface with the contacting vertebral bodies to facilitate maintaining the spacer in place. The beads are preferably composed of titanium or a titanium alloy (such as Ti-6Al-4V) which is non-reactive within the body. Since the early 1970's, titanium and titanium alloys have been approved by the United States Food and Drug Administration for use in knee, shoulder, and hip implants to promote bone ingrowth.

It has been found that beads of a certain size range are preferred. Suitable small beads will have a mesh size of −45 +60 (0.009 inch to 0.011 inch). Suitable medium beads will have a mesh size of −25 +30 (0.016 inch to 0.027 inch). Suitable large beads will have a mesh size of −18 +30 (0.032 to 0.046 inch). The size of the beads determines the porosity of the finished spacer 10. The larger the beads, the greater the porosity. In certain applications, it may be desirable to mix beads of various sizes to obtain a finished spacer 10 having a variable porosity.

It is possible to intermix strips, or strands, of titanium wire mesh with the beads to form a spacer 10 having variable qualities of strength and porosity. In general, the use of titanium wire mesh results in a stronger, less porous spacer 10. It also is possible to form the spacer 10 entirely of titanium wire mesh. Such mesh presently is used as a porous coating for knee, shoulder, and hip implants. Such mesh sometimes is referred to a spaghetti mesh, and is commercially available from the Zimmer Company of Warsaw, Ind.

One suitable method of fusing titanium beads to form the spacer 10 includes placing the beads into a cavity within a substantially purified graphite mold. The mold is preferably a three piece mold forming a cavity of the finished dimensions of the spacer 10. The mold containing the titanium beads is then heated to a high temperature, for example, 2000 degrees F. or higher until the sintering is complete, around 24 hours. Other conventional methods for fusing titanium or other beads which provide a sufficiently strong spacer 10 also may be acceptable. When titanium spaghetti mesh is used to form the spacer 10, the strands of mesh are placed in the mold in a tangled, tortuous mass. Sintering produces strong inter-strand bonds with variably sized openings to form a spacer 10 of suitable strength and porosity.

The procedure for fusing two or more vertebrae together using the spacer 10 of the invention is substantially the same as the procedure for fusing vertebrae using a bone graft, but without many of the complications due to obtaining a suitable bone graft and the possibility of transmitting disease from the bone graft donor. One anterior procedure for implanting a bone graft to fuse vertebra of the lumbar spine is discussed in Collis et al., "Anterior Total Disc Replacement: A Modified Anterior Lumbar Interbody Fusion," Lumbar Interbody Fusion, ed. Robert Watkins, Chapter 13, pp. 149–152, Aspen Publications (1989), the disclosure of which is incorporated herein by reference.

Figure 2:
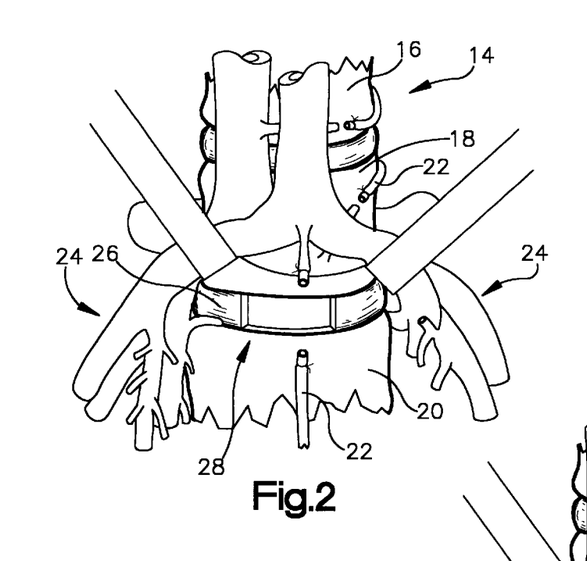
FIG. 2 is an elevational view of the anterior of a portion of the lumbar spine and sacrum illustrating a graft bed.
Figure 3:
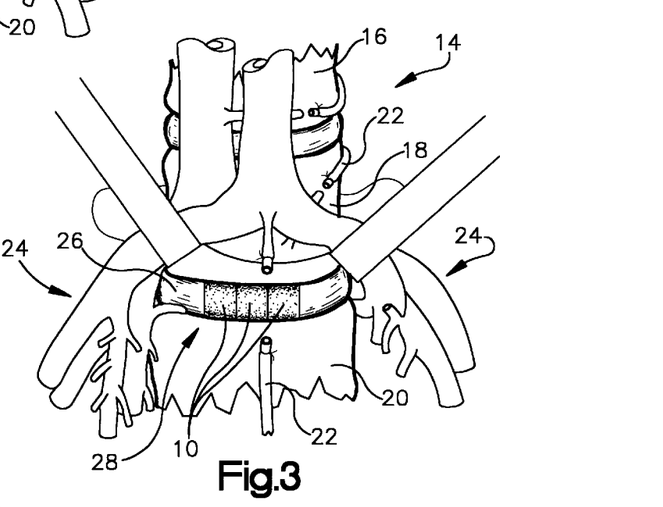
FIG. 3 is a view similar to FIG. 2 showing spacers according to the invention implanted in the graft bed.

Referring to FIGS. 2 and 3, there is shown an anterior elevation view of the lumbar spine 14 including the fourth and fifth lumbar vertebrae 16, 18, respectively, and the sacrum 20 with the sacral vessels 22 ligated and both iliac vessels 24 retracted outwardly to expose the vertebral disc 26 between the fifth lumbar vertebra 18 and the sacrum 20. As an example, to fuse the fifth lumbar vertebra 18 to the sacrum 20, using an anterior approach, a graft bed 28 is prepared by surgically exposing the affected area and excising portions of the vertebral body of the vertebra 18 and the sacrum 20 and the section of the disc 24 located therebetween, as shown in FIG. 2. An appropriate number of spacers 10, in this example, three, are then implanted into the graft bed 28. Over time bony tissue ingrowth will desirably fuse the vertebral bodies of the vertebra 18 and the sacrum 20 to the spacers 10 and thus fuse the vertebra to the sacrum through the spacers. The number of spacers 10 employed will be a function of a number of factors, including the particular vertebrae to be fused and the deterioration of the vertebral disc and of the vertebral bodies themselves.

Figure 4:
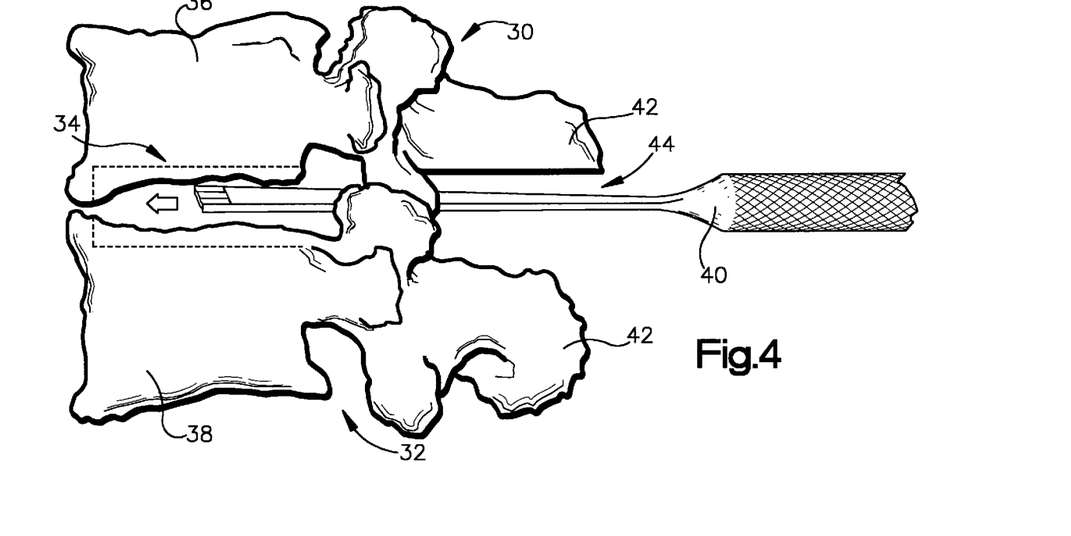
FIG. 4 is a side elevational view of two representative lumbar vertebrae illustrating the location of a posterior-formed graft bed.
Figure 5:
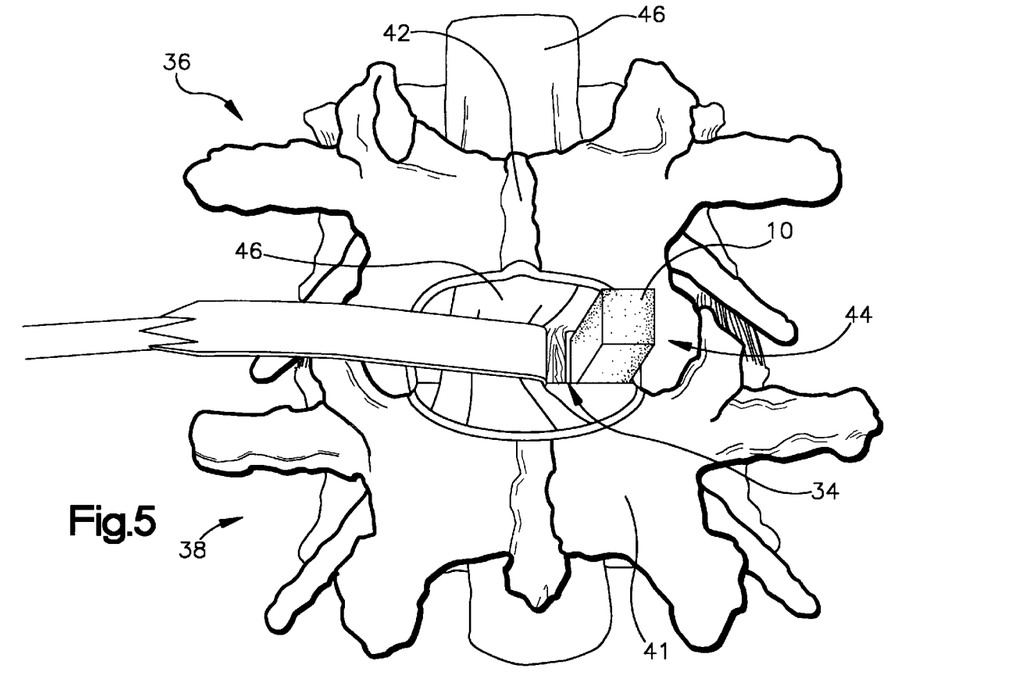
FIG. 5 is an elevational view of the posterior of representative lumbar vertebrae illustrating the locations of separate posteriorly formed graft beds.
Figure 6:
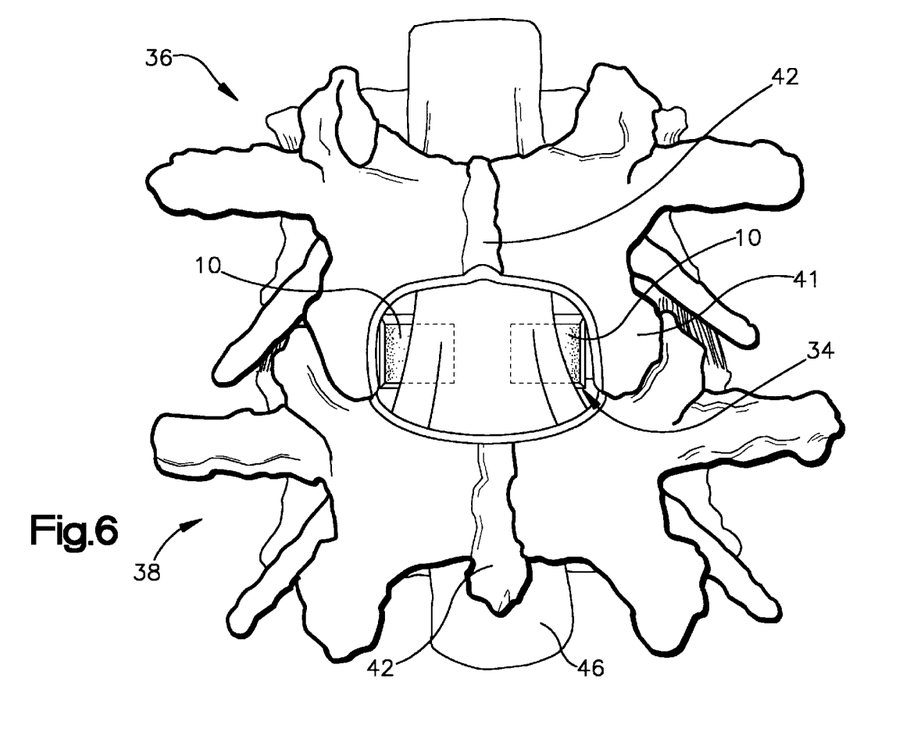
FIG. 6 is a view similar to FIG. 5 showing two spacers according to the invention implanted in the graft beds.

The intervertebral spacers 10 may also be implanted through known posterior approaches. In a typical procedure using a posterior approach in which two spacers are implanted, such as is shown in FIGS. 4 through 6 which represent side and rear elevations of two representative lumbar vertebrae 30, 32, the posterior portion of the subject area of the lumbar spine is surgically exposed. Graft beds 34 are then formed by excising the required portions of adjacent vertebral bodies 36, 38 of the vertebrae 30, 32, respectively, and a section of the disc located therebetween. The graft beds 34 may be formed using a cutting tool 40, such as is shown in FIG. 4 (FIG. 4 omits the Canda Equina and the disc for clarity), wherein portions of the lamina 41 and/or spinous process 42 of one or both of the vertebrae are removed to open a passage 44 through which the tool may be inserted to reach the vertebral bodies. To implant the spacers 10 once the graft beds 34 have been formed, the Canda Equina and protective dura 46 are first retracted to one side to expose a graft bed and a spacer is inserted into the exposed graft bed (see FIG. 5), and then the Canda Equina and dura are retracted to the other side to insert a spacer into the exposed other graft bed.

Figures 9A, 9B, 9C, 9D, 9E:
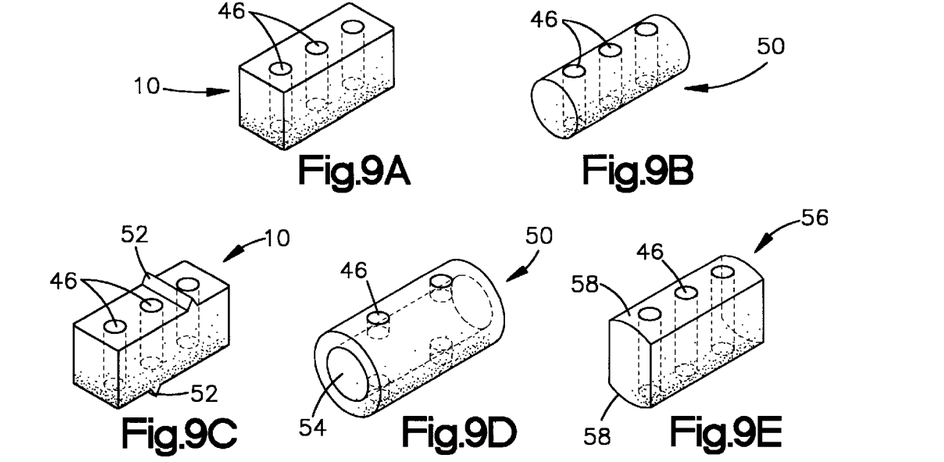
FIG. 9A is a perspective view similar to FIG. 1, showing a spacer provided with a plurality of parallel apertures opening through the top and bottom faces of the spacer.
FIG. 9B is a perspective view of an intervertebral spacer in accordance with the invention, the spacer being in the form of a cylinder and including a plurality of apertures that are disposed parallel to the end faces of the cylinder.
FIG. 9C is a view similar to FIG. 9A, showing the use of external teeth, or ribs.
FIG. 9D is a view similar to FIG. 9B in which a large cylindrical opening extends longitudinally through the center of the spacer.
FIG. 9E is a view similar to FIG. 9A in which the top and bottom faces of the spacer are rounded.

Referring now to FIGS. 9A–9N, the spacer according to the invention is shown in a variety of configurations. In all of these configurations, the spacer is formed by sintering titanium or titanium alloy beads or spaghetti mesh within a suitably configured mold. In particular, FIG. 9A shows the spacer 10 provided with a plurality of parallel, equidistantly spaced apertures 46. The apertures 46 open through the top and bottom faces of the spacer 10. It also is possible to provide a longitudinally extending opening (not shown) that opens through the end faces of the spacer 10.

The spacer 10 can be provided in various sizes. A typical size is 10 mm wide, 27 mm long, and a variable height of 12, 14, 16 or 18 mm. The spacer 10 can be provided in shorter lengths of 24 mm, or longer lengths of 30 mm. For those spacers 10 having a width of 10 mm, the apertures 46 should have a diameter of about 0.1875 inch.

The spacer 10 also can be provided in the different widths, for example, 13 mm. With a width of 13 mm, variable lengths of 24, 27 or 30 can be provided. The height also can be selected among 12, 14, 16 or 18 mm. For spacers 10 having a width of 13 mm, the apertures 46 should have a diameter of 0.2188 inch.

Referring now to FIG. 9B, a spacer 50 in the form of a cylinder is shown. The spacer 50 is provided in various diameters and lengths, for example, 10 mm, 12 mm, 14 mm and 16 mm diameter, and lengths of 24, 27 and 30 mm. As with the spacer 10, three equidistantly spaced apertures 46 are provided for the spacer 50. For spacers 50 having diameters of 10 or 12 mm, the apertures 46 have a diameter of about 0.1875 inch, while for spacers 50 having a diameter of 14 or 16 mm, the apertures 46 have a diameter of about 0.2188 inch.

Referring now to FIG. 9C, the spacer 10 is provided with laterally extending teeth or ribs 52. In cross section, the ribs 52 are triangular with a vertex angle of 60 degrees and a height of 2 mm. The ribs 52 prevent undesired movement of the spacer 10 within the patient after the spacer 10 has been implanted in the graft bed 28.

Referring to FIG. 9D, the spacer 50 is shown with two spaced-apart apertures 46. The spacer 50 also is provided with a longitudinally extending aperture 54 that opens through the end faces of the spacer 50. The diameter of the aperture 54 is selected such that the wall thickness of the spacer 50 is approximately 3 mm.

Referring now to FIG. 9E, the spacer 56 is similar to the spacer 10, but includes flat, parallel end faces and sidewalls, and rounded top and bottom faces 58. As with the spacer 10, a plurality of apertures 46 are provided for the spacer 56. The dimensions for the width, length, and height of the spacer 56 are the same as those described previously for the spacer 10. The radius for the top and bottom faces 58 should be approximately 9 mm.

Figure 9F:
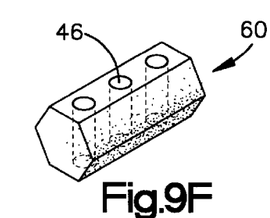
FIG. 9F is a perspective view of a intervertebral spacer according to the invention, the spacer being in the form of a hexagonal prism with apertures opening through the top and bottom faces.
Figure 9G:
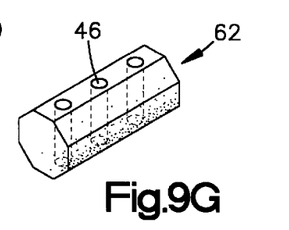
FIG. 9G is a view similar to FIG. 9F in which the spacer is in the form of an octagonal prism with apertures opening through the top and bottom faces.
Figure 9H:
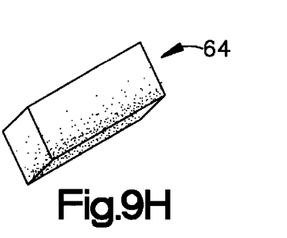
FIG. 9H is a view similar to FIG. 9F in which the end faces are rhombuses.

Referring now to FIGS. 9F, 9G and 9H, spacers 60, 62 and 64 are illustrated. The spacer 60 is a hexagonal prism, the spacer 62 is an octagonal prism, and the spacer 64 is a rhomboidal prism. The spacers 60, 62, as with the spacer 10, are provided with a plurality of parallel, equidistantly spaced apertures 46. If desired, the spacers 60, 62 and 64 could be provided with longitudinally extending openings such as the opening 54 included as part of the spacer 50. In general, the spacer according to the invention can be provided in a variety of geometric configurations. Virtually any polyhedron prism will provide satisfactory results.

Figure 9I:
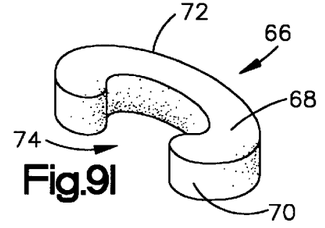
FIG. 9I is a perspective view of a plate-like intervertebral spacer which, when viewed from above, is generally C-shaped.
Figure 9J:
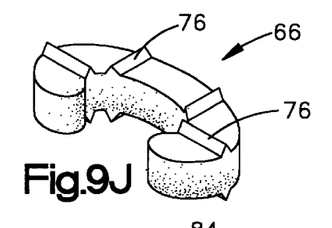
FIG. 9J is a view similar to FIG. 9I in which ribs have been added to the upper and lower faces of the spacer.

Referring to FIGS. 9I–9N, a variety of plate-like spacers are shown. The spacers are provided in a variety of lengths, widths, and depths to fit all male and female vertebral bodies. In FIG. 9I, a spacer 66 includes flat, parallel upper and lower faces 68, 70 with a rounded exterior surface 72 and a cut-out portion 74. The spacer 66 generally is C-shaped. In FIG. 9J, the spacer 66 is provided with a plurality of ribs 76 that are similar in size and shape to the ribs 52 and which perform the same function.

Figure 9K:
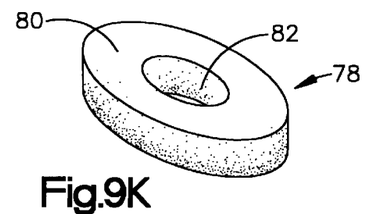
FIG. 9K is a view similar to FIG. 9I showing an elliptical spacer with an elliptical opening at its center.
Figure 9L:
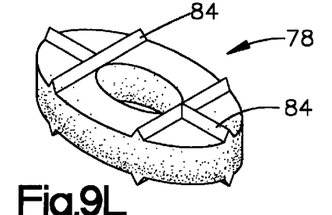
FIG. 9L is a view similar to FIG. 9K in which ribs have been added to the upper and lower faces of the spacer.

In FIG. 9K, a spacer 78 includes an elliptical body portion 80 with an elliptical opening 82 at its center. In FIG. 9L, the spacer 78 is provided with ribs 84 of the same size and shape as the ribs 52.

Referring to 9M, a spacer 86 includes a kidney-shaped body portion 88 having a small cut-out portion 90. In FIG. 9N the spacer 86 is provided with ribs 92 that are the same size and shape as the ribs 52.

It is expected that the spacers 66, 78, 86 will be provided in sizes large enough to perform the function of two or three spacers 10 or 50. It is expected that a single, large graft bed 28 will be formed such that the spacer 68, 78, 86 will fill the graft bed 28 entirely.

Figure 7:
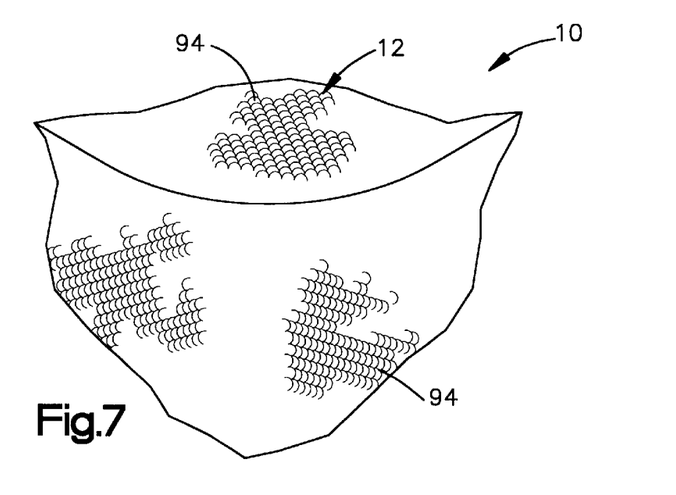
FIG. 7 is an enlarged view of the surface of the spacer of FIG. 1.
Figure 8:
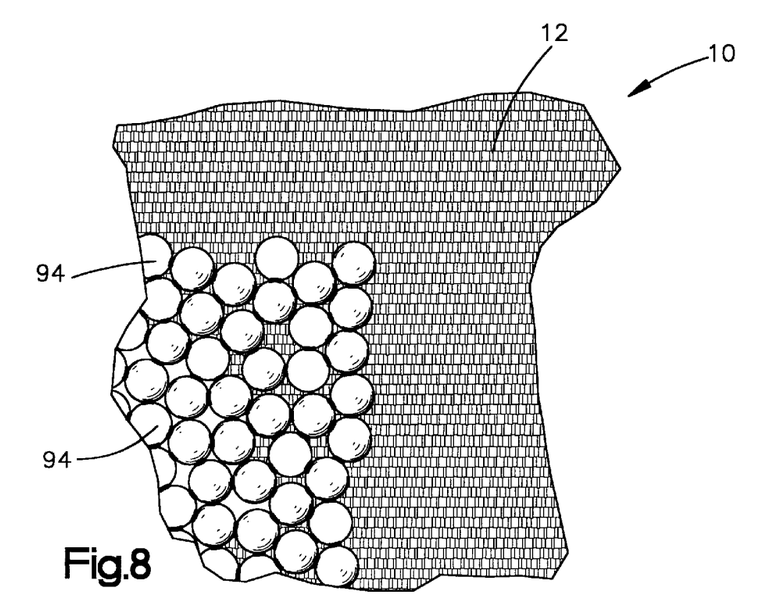
FIG. 8 is a view similar to FIG. 7 showing the surface enlarged to an even greater extent.
Figure 10:
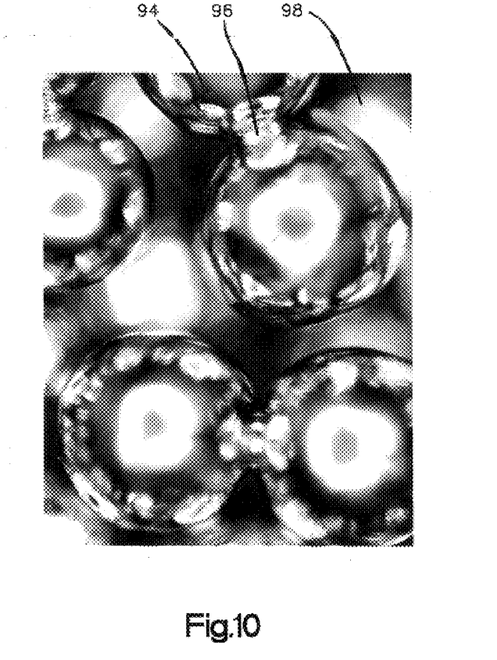
FIG. 10 is a photomicrograph of a portion of an intervertebral spacer according to the invention showing sintered beads of a mesh size of −30 +45 at a magnification of 100×.
Figure 11:
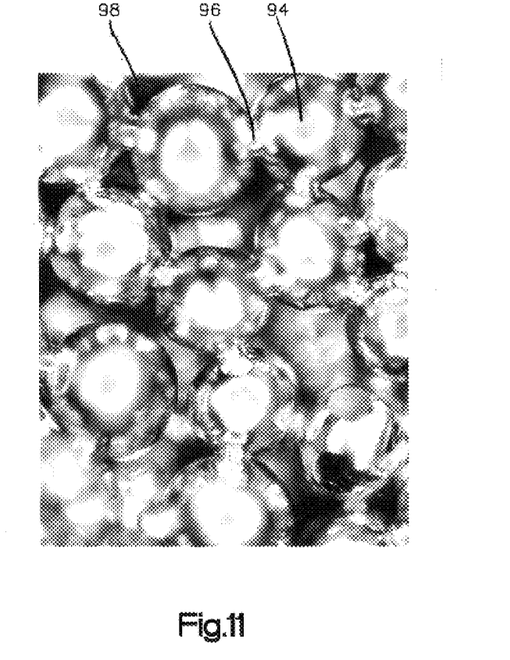
FIG. 11 is a photomicrograph similar to FIG. 10 showing sintered beads of a mesh size of −45 +60 at a magnification of 100×.
Figure 12:
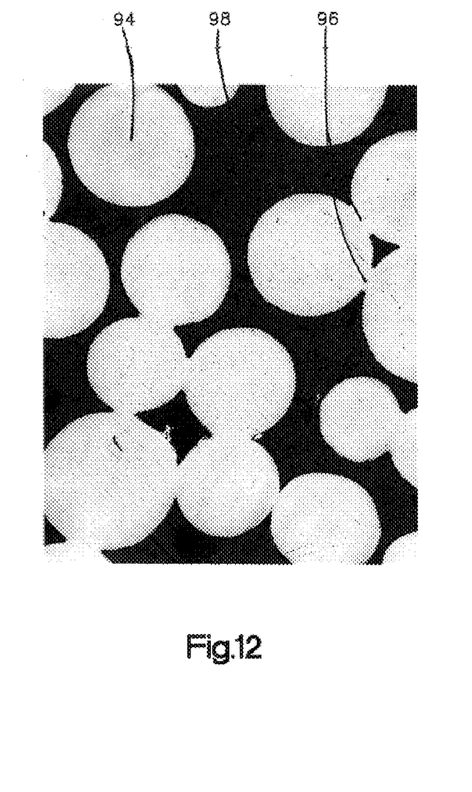
FIG. 12 is a photomicrograph showing a cross-sectional view of an intervertebral spacer according to the invention, wherein beads of a mesh size of −45 +60 are shown at a magnification of 100×.
Figure 13:
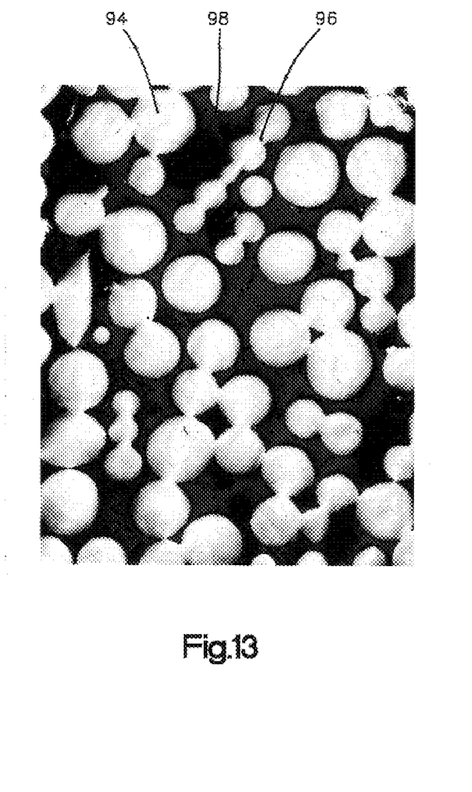
FIG. 13 is a photomicrograph similar to FIG. 12 showing a cross-sectional view of beads of a mesh size of −45 +60 at a magnification of 50×.

Referring now to FIGS. 7 and 8, the relationship among the beads that comprise the spacer according to the invention is illustrated schematically. In FIGS. 10–12, photomicrographs illustrate titanium or titanium alloy beads 94 sintered together to form the spacer according to the invention. FIG. 10 is a photograph of beads 94 having a mesh size of –30 +45 at a magnification of 100×. FIG. 11 shows beads 94 having a mesh size of –45 +60 at a magnification of 100×. FIG. 12 shows a cross-sectional view of the same beads as FIG. 11 at a magnification of 100×, while FIG. 13 shows a cross-sectional view of beads having a mesh size of –45 +60 at a magnification of 50×.

In FIGS. 10–12, bonds between adjacent beads 94 are indicated by the reference numeral 96. Spaces among adjacent beads 94 are indicated by the reference numeral 98. The construction illustrated in FIGS. 10–12 is quite strong due to the inherent strength of the beads 94, as well as the welds that define the sintered bonds 96 between adjacent beads 94.

Although the invention has been shown and described with respect to a certain preferred embodiment, it is obvious that equivalent alterations and modifications will occur to others skilled in the art upon reading and understanding this specification. The present invention includes all such equivalent alterations and modifications and is limited only by the scope of the following claims.

What is claimed is:

1. An intervertebral spacer that is porous throughtout consisting essentially of a plurality of fused, generally spherical beads of a biologically inert material selected from the group consisting of substantially pure titanium and a titanium alloy.

2. The spacer of claim 1, wherein the beads occupy a range of generally 45 to 58 percent of the volume of the spacer.

3. The spacer of claim 1, wherein the beads are fused by sintering.

4. The spacer of claim 1, wherein the porosity of the spacer is sufficient to facilitate tissue ingrowth and bony fusion.

5. The spacer of claim 1, wherein the spacer is in the form of a prism having end faces.

6. The spacer of claim 5, wherein the end faces of the prism are selected from the group consisting of a square, a rectangle, a triangle, a hexagon, an octagon, a rhombus, a rhomboid, and a trapezoid.

7. The spacer of claim 1, wherein the spacer is of a generally rectangular shape having opposed, substantially parallel end faces, side faces, and top and bottom faces.

8. The spacer of claim 7, further comprising at least one aperture extending through the spacer and opening through the top and bottom faces.

9. The spacer of claim 8, wherein three apertures are provided, the apertures being spaced equidistantly from each other.

10. The spacer of claim 7, further comprising a second aperture extending through the spacer, the second aperture opening through the end faces.

11. The spacer of claim 7, further comprising ribs formed on the top and bottom faces, the ribs, in cross-section, being generally triangular and extending generally parallel to the end faces.

12. The spacer of claim 1, wherein the spacer is of a generally cylindrical shape having a longitudinal axis and end faces that are parallel to each other.

13. The spacer of claim 12, further comprising at least one aperture extending through the spacer parallel to the end faces.

14. The spacer of claim 13, wherein three apertures are provided, the apertures being spaced equidistantly from each other.

15. The spacer of claim 12, further comprising a large round aperture extending through the spacer parallel to, and concentric with, the longitudinal access, the large round aperture defining a wall thickness of the spacer.

16. The spacer of claim 15, wherein the wall thickness of the spacer is approximately 3 mm.

17. The spacer of claim 15, further comprising at least one aperture extending through the spacer parallel to the end faces.

18. The spacer of claim 16, wherein three apertures are provided, the apertures being spaced equidistantly from each other.

19. The spacer of claim 1, wherein the spacer is of a combined rectangular-cylindrical shape, with opposed, flat end faces that are parallel to each other, opposed, flat side faces that are parallel to each other, and opposed, rounded top and bottom faces.

20. The spacer of claim 19, further comprising at least one aperture extending through the spacer and opening through the top and bottom faces.

21. The spacer of claim 20, wherein three apertures are provided, the apertures being spaced equidistantly from each other.

22. The spacer of claim 19, further comprising a second aperture extending through the spacer, the second aperture opening through the end faces.

23. The spacer of claim 19, further comprising ribs formed on the top and bottom faces, the ribs, in cross-section, being generally triangular and extending generally parallel to the end faces.

24. The spacer of claim 1, wherein the spacer is in the form of a plate having flat, generally parallel upper and lower faces.

25. The spacer of claim 24, wherein the spacer, when viewed from above, is generally C-shaped.

26. The spacer of claim 24, wherein the spacer, when viewed from above, is elliptical with an elliptical opening at its center.

27. The spacer of claim 24, wherein the spacer, when viewed from above, is kidney-shaped.

28. The spacer of claim 24, further comprising ribs formed on the upper and lower faces.

29. The spacer of claim 28, wherein the ribs, in cross-section, are generally triangular.

30. A method of fusing adjacent vertebrae of the spine comprising the steps of:
  excising a portion of an intervertebral disc separating adjacent vertebra and portions of the adjacent vertebrae to define a graft bed, and
  inserting into the graft bed at least one porous intervertebral spacer that is porous throughtout consisting essentially of a plurality of fused, generally spherical beads of a biologically inert material selected from the group consisting of substantially pure titanium and a titanium alloy.

31. The method of claim 30, wherein the beads occupy a range of generally 45 to 58 percent of the volume of the spacer.

32. The method of claim 30, wherein the beads are fused by sintering.

33. The method of claim 30, wherein the graft bed is formed by an excision from the posterior of the spine.

34. The method of claim 30, wherein the graft bed is formed by an excision from the anterior of the spine.

* * * * *